United States Patent
Weber et al.

(12)

(10) Patent No.: US 6,657,087 B2
(45) Date of Patent: Dec. 2, 2003

(54) PROCESS AND APPARATUS FOR THE WORK-UP BY DISTILLATION OF CLEAVAGE PRODUCT MIXTURES PRODUCED IN THE CLEAVAGE OF ALKYLARYL HYDROPEROXIDES

(75) Inventors: Markus Weber, Haltern (DE); Christoph Schwarz, Marl (DE); Uwe Tanger, Bochum (DE); Hermann-Josef Korte, Haltern (DE); Jochen Ullrich, Gladbeck (DE)

(73) Assignee: INEOS Phenol GmbH & Co. KG, Gladbeck (DE)

( * ) Notice: Subject to any disclaimer, the term of this patent is extended or adjusted under 35 U.S.C. 154(b) by 0 days.

(21) Appl. No.: 09/986,904

(22) Filed: Nov. 13, 2001

(65) Prior Publication Data

US 2002/0068840 A1 Jun. 6, 2002

(30) Foreign Application Priority Data

Dec. 6, 2000 (DE) .......................... 100 60 503

(51) Int. Cl.[7] .......................... C07C 45/41; C07C 37/68
(52) U.S. Cl. ....................... 568/385; 568/386; 568/389; 568/397; 568/411; 568/754
(58) Field of Search ................. 568/385, 386, 568/389, 397, 411, 754

(56) References Cited

U.S. PATENT DOCUMENTS 4,262,150 A * 4/1981 Pujado
4,298,765 A * 11/1981 Cochran et al.
5,064,507 A * 11/1991 O'Donnell et al.

FOREIGN PATENT DOCUMENTS

EP          0 028 910          5/1981

* cited by examiner

Primary Examiner—Samuel Barts
Assistant Examiner—Sikarl A. Witherspoon
(74) Attorney, Agent, or Firm—Oblon, Spivak, McClelland, Maier & Neustadt, P.C.

(57) ABSTRACT

The present invention claims a process and an apparatus for the work-up by distillation of cleavage product mixtures produced in the cleavage of alkylaryl hydroperoxides. Usually, in the work-up by distillation of cleavage product mixtures which are produced in the cleavage of alkylaryl hydroperoxides, the cleavage product mixture is divided into three main fractions, for which at least two distillation columns are used. The use of two distillation columns has the disadvantage that the capital costs, and also the energy costs, in these conventional processes are relatively high.

Figure 1:
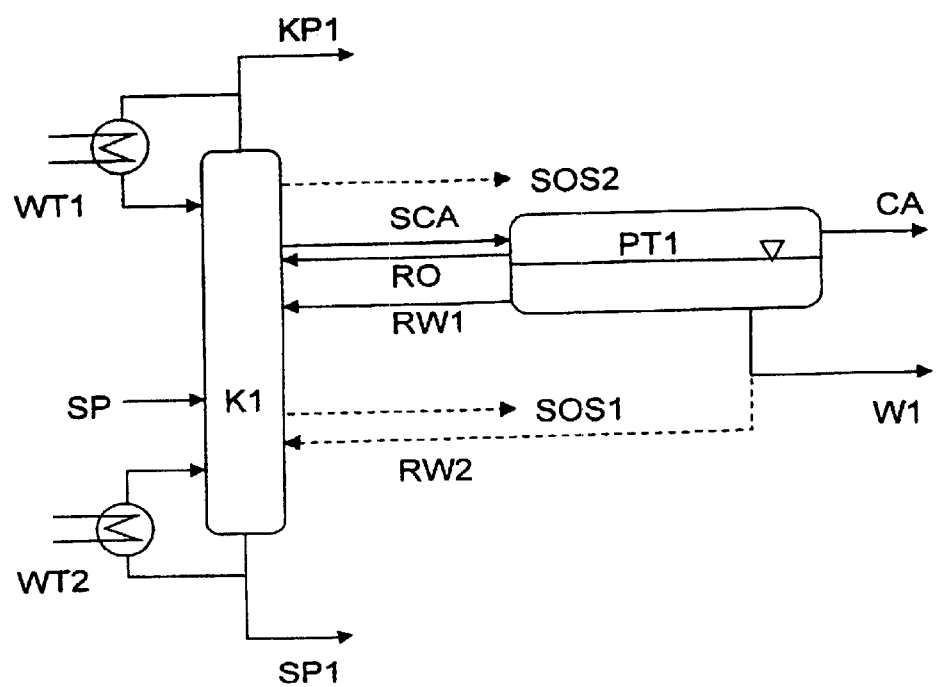

By means of the inventive process for the work-up by distillation of cleavage product mixtures, the equipment requirements and the energy consumption can be markedly reduced in comparison with customary plants, since the cleavage product mixture can be resolved into the three main fractions in only one apparatus. The inventive process can be used for the work-up by distillation of cleavage product mixtures produced in the cleavage of alkylaryl hydroperoxides, in particular in the cleavage of cumene hydroperoxide. By using the inventive process it is possible to separate off phenol and acetone from a cleavage product mixture that was obtained in the cleavage of cumene hydroperoxide.

29 Claims, 2 Drawing Sheets

PROCESS AND APPARATUS FOR THE WORK-UP BY DISTILLATION OF CLEAVAGE PRODUCT MIXTURES PRODUCED IN THE CLEAVAGE OF ALKYLARYL HYDROPEROXIDES

The invention relates to an improved process for the work-up by distillation of cleavage product mixtures produced in the cleavage of alkylaryl hydroperoxides. In particular, the present invention relates to a process for the work-up by distillation of cleavage product produced in the cleavage of cumene hydroperoxide.

The process of acid-catalyzed cleavage of cumene hydroperoxide into phenol and acetone has long been of particular industrial importance. In this preparation of phenol from cumene by the Hock process, in a first reaction stage, the oxidation, cumene is oxidized to cumene hydroperoxide (CHP) and the CHP is then concentrated in a vacuum distillation, the concentration stage, to 65 to 90% by weight. In a second reaction stage, cleavage, the CHP is cleaved into phenol and acetone by the action of an acid, usually sulfuric acid. In addition to phenol and acetone the cleavage product has other compounds which can be formed in the reaction steps preceding the cleavage and which are not converted, or are only partially converted, in the cleavage. The most important compounds which can be present in the cleavage product in addition to phenol and acetone are, in particular, α-methylstyrene (AMS), cumene and acetophenone. In addition, small amounts of dimethyl phenyl carbinol (DMPC) already formed in the oxidation may be present in the cleavage product. Further impurities comprise compounds such as methylbenzofuran (MBF), hydroxyacetone, mesityl oxide (MO) and carbonyl compounds such as (acet) aldehydes and 2-phenylpropionaldehyde, for example. After neutralizing the cleavage product and any removal of an aqueous phase, the cleavage product is worked up by distillation.

Various processes for work-up of the cleavage product by distillation are known (Ullmann's Encyclopedia of Industrial Chemistry, 5th completely revised edition, Vol. A19, 1991, VCH Verlagsgesellschaft mbH, Weinheim). In principle, in all these processes, the cleavage product is first neutralized, with aqueous sodium hydroxide solution, amines, aqueous phenolate lye and/or ion exchanger resin being used. After a phase separation, the organic part of the neutralized cleavage product is transferred to a first column in which crude acetone, which can contain water, hydroxyacetone, cumene and/or AMS, is distilled off overhead from the residual cleavage product. This crude acetone is usually treated with alkali in a washer and again purified by distillation. However, in part, the wash also takes place in the column. The bottoms product produced in the first column is distilled in a second column, residual AMS and cumene being taken off from this column overhead and usually being fed to a hydrogenation in which cumene is again prepared. AMS and cumene can also be separated off in an azeotropic distillation with water. The bottoms product remaining in the second column is distilled in a crude phenol column.

The resultant crude phenol can be further purified by an extractive distillation with water and/or by treatment with an acid ion exchanger and subsequent distillation. In the latter process compounds which are difficult to separate from phenol by distillation, for example mesityl oxide and hydroxyacetone, are condensed to form higher-boiling compounds.

In DE-AS 1 105 878 (phenol chemistry) also, the neutralized cleavage product which is separated off from the crude acetone in a crude acetone column is transferred into a hydrocarbon column in which, in the presence of water, hydrocarbons boiling lower than phenol, such as AMS and cumene are distilled off overhead. From the bottom of the column the organic phase is taken off and applied to the top of a downstream column in which water is separated off from phenol and high-boilers which are produced in the bottom of the column. The mixture of phenol and high-boilers is then transferred to a crude phenol column. The residues produced in the crude phenol column and in the pure phenol distillation can then be fed to a cracking still in which the residues are worked up and one part of phenol is recovered. These recovered products of value can again be transferred to the hydrocarbon column.

EP 0 032 255 (UOP) describes a process for working up cleavage product in which the organic part of a virtually neutralized (pH≈6) cleavage product is again washed with water and then the organic part is transferred to a crude acetone column in which the crude acetone is separated off from the remaining cleavage product. The residue remaining in the bottom phase is transferred directly to a cumene column in which the crude phenol is produced as bottoms product which in turn is fed to a purifying distillation. The mixture taken off overhead from the cumene column, which contains principally AMS, cumene and water, is transferred to a phase-separation vessel in which an aqueous phase is separated off. The resultant organic phase is transferred to a washing column in which the organic mixture is treated with sodium hydroxide solution in order to remove any phenol still present from the mixture of AMS and cumene as sodium phenoxide. The mixture of AMS and cumene which has been freed from phenol is fed via the top of the column to a hydrogenation. In U.S. Pat. No. 4,262,150 (UOP), also, the same column circuit is used as described in EP 0 032 255 (UOP). The difference from EP 0 032 255 is that, to neutralize the cleavage product, an extraction column is used instead of one or more combinations of mixers and phase-separation apparatuses.

U.S. Pat. No. 3,322 651 (UOP) describes the use of nitrogen compounds, in particular amines, for purifying phenol obtained in the cleavage of CHP.

U.S. Pat. No. 5,510,543 (GE) describes a process for working up the cleavage product from CHP cleavage, in which the cleavage product is adjusted to a pH of 4.0 to 4.9 in a neutralizer by adding a base, in particular sodium hydroxide solution. In the neutralizer the cleavage product is separated into an aqueous phase and an organic phase. The organic phase is transferred to a column termed the splitter in which the cleavage product is separated by distillation into an acetone-rich fraction and a phenol-rich fraction. The phenol-rich fraction is taken off at the bottom of the column and fed to a phenol purification, which can consist, for example, of one or more further distillations. The acetone-rich fraction is taken off at the top of the column and fed to an acetone column, in which case base is added to this fraction before entry into the column in such an amount that the fraction has a pH of approximately 9, so that the organic acids which are also present in this fraction are neutralized. The mixture arising in the bottom phase of the column which, in addition to water, also contains hydrocarbons and the salts of organic acids, is transferred to a phase-separation apparatus in which this mixture is separated into an organic phase and an aqueous phase. The organic phase can be treated again for recovery of cumene.

Furthermore, processes have been developed in which individual fractions which arise in the work-up by distillation of cleavage product are treated specifically. Thus, U.S.

Pat. No. 5,487,816 (UOP) describes a process for separating off AMS from a mixture which contains phenol, AMS and water and which arises as bottom product of a crude acetone column. The crude acetone column is operated in this case in such a manner that cumene is taken off from the cleavage product at the top of the crude acetone column together with the acetone. The mixture containing AMS and phenol is separated in a column in such a manner that in the bottom of the column predominantly phenol is produced, which can be fed to further work-up, and at the top of the column a mixture of AMS, water and smaller amounts of phenol is taken off, which mixture is condensed and adjusted to a pH above 6 by adding a basic reagent. This achieves the phenol being principally present in the aqueous phase, while the AMS is present in an organic phase in which only small amounts of phenol are present as impurity. The phases are separated from one another by a phase-separation apparatus. The organic phase can be fed to a hydrogenation, while the aqueous phase can be fed back to the column as reflux.

In U.S. Pat. No. 4,370,205 (UOP), the stream taken off from the bottom of the crude acetone column also still contains cumene, in contrast to the process described in U.S. Pat. No. 5,487,816 (UOP). Against this background a different column circuit is proposed. In particular two columns operated under virtually the same conditions are used in which the bottoms product produced is predominantly phenol, whereas predominantly AMS and cumene are taken off overhead. The crude phenol taken off as bottoms product in the first column is fed to further work-up steps, and the crude phenol taken off as bottoms product in the second column is fed back to the first column. The overhead product of the second column is treated with sodium hydroxide solution in a wash column. The overhead product of this column, which comprises AMS and cumene, can be fed to the hydrogenation.

In U.S. Pat. No. 4,251,325 (BP Chemicals), the work-up of a fraction which has been freed from low-boilers and acetone is optimized such that the cumene column is operated in such a manner that at the top a mixture is taken off which comprises cumene, AMS and hydroxyacetone, where the latter is virtually completely separated off from residual crude phenol, and thus need not be separated off in a complex manner during the phenol work-up.

U.S. Pat. No. 4,333,801 (UOP) describes the work-up of a fraction which comprises AMS, cumene, phenol, water and impurities, for example hydroxyacetone. This process is chiefly concerned with removing an AMS/cumene fraction, which has a very low phenol concentration, from the total fraction. This is achieved by operating the cumene column in such a manner that a mixture of cumene and AMS is taken off overhead from the column, which mixture is condensed and run into a phase-separation vessel. Any water possibly present is separated off and discarded. A portion of the organic phase is fed back to the column top as reflux. Another portion of the organic phase is fed to a washer in which phenol residues which would interfere with the hydrogenation are removed from the phase so that this phase can be fed to the hydrogenation. From a side stream takeoff of the cumene column there is taken off a fraction comprising AMS and cumene and an azeotropic mixture of water and phenol, which fraction is also condensed and transferred to a phase-separation vessel. The aqueous phase which can comprise phenol is fed to a work-up stage. The organic phase which comprises cumene, AMS and as much phenol as remains in the organic phase in accordance with the phase equilibrium between the organic and aqueous phases is evaporated and fed back in the vaporous state into the cumene column above the side stream takeoff. A crude phenol fraction is taken off from the bottom of the column.

A further process is described in U.S. Pat. No. 5,064,507 (Allied). In this process the cleavage product is first separated from the crude acetone in a crude acetone column. The bottoms product is transferred to a cumene column in which cumene and AMS are removed from the cleavage product. The column is, however, operated in such a manner that a certain portion of AMS is still present in the bottoms product, since this is required as a reaction partner or solvent in the further work-up of the phenol to remove MBF and other impurities. This bottoms product is reacted with an amine, preferably hexamethylenediamine, in a reactor having plug flow characteristics to convert carbonyl impurities, for example acetol (hydroxyacetone, HA) or MO, into higher-boiling compounds. The product thus treated is further worked up by distillation. By the purified end product phenol, flow will have passed through a further four columns and two reaction zones.

U.S. Pat. No. 5,131,984 (Allied) describes the work-up by distillation of crude phenol, which has been separated from the predominant portion of acetone, cumene and AMS. This crude phenol is treated in a vacuum distillation column in such a manner that a vaporous mixture which comprises phenol and low-boilers is taken off at the top of the column. This mixture is run into a condenser in which the predominant portion of the vaporous mixture is condensed. The condensed portion of the mixture is run back into the column, in which case the purity of the phenol taken off as product was a function of whether the condensate was fed back into the column at the top or below the top. The vaporous portion which, inter alia, comprises low-boilers and acids, is fed to a further treatment, for example a further distillation column. A phenol-comprising fraction, which can be further worked up, is taken off from the vacuum distillation column, from a side stream takeoff which is disposed at least one theoretical stage below the top of the column.

A similar process is described in U.S. Pat. No. 5,122,234 (Allied) with the difference that water is additionally run into the column and at the top of the column a mixture which predominantly comprises water and phenol is taken off, which mixture is partly condensed and returned to the column.

All known processes for work-up by distillation of cleavage product are relatively complex, since usually two distillation columns alone are required for separating the main constituents of the cleavage product into three main fractions, crude acetone, AMS/cumene and crude phenol. Further work-up of the main fractions to remove unwanted byproducts, for example water, requires a lot of equipment. All the processes currently used have a relatively high energy consumption, in particular a high steam consumption. Since the production of phenol comprises several million metric tons per year, even small savings in costs of energy or capital costs can be critical for the competitiveness of a process.

The object of the present invention was therefore to provide a process for work-up by distillation of cleavage product from the cleavage of cumene hydroperoxide in which, with a small energy consumption and low requirements of equipment, the main products acetone, cumene/AMS and phenol can be separated from one another and from unwanted byproducts.

Surprisingly, it has been found that by separating the cleavage product by distillation into three main fractions in a single distillation step the main products can be effectively separated from one another with a lower energy consumption and lower equipment requirements than in customary processes and the removal of unwanted byproducts is also simplified.

The present invention therefore relates to a process according to claim 1 for the work-up by distillation of cleavage product produced in the cleavage of alkylaryl hydroperoxides, which comprises resolving the cleavage product into at least three fractions in a single distillation step.

The present invention also relates to a distillation column for the separation by distillation of cleavage product mixtures from cumene hydroperoxide cleavage as claimed in claim 15, which is dimensioned such that a crude acetone fraction comprising at least 75% by weight of acetone can be taken off at the top of the column, a crude phenol fraction comprising at least 75% by weight of phenol can be taken off at the bottom of the column and a fraction which comprises at least hydroxyacetone and cumene and/or α-methylstyrene can be taken off from the side of the column.

The present invention also relates to a process as claimed in claim 21 for preparing phenol and acetone which comprises the steps oxidation of cumene to cumene hydroperoxide cleavage of cumene hydroperoxide work-up by distillation of the cleavage product mixture produced in the cleavage of cumene hydroperoxide, which comprises resolving the cleavage product mixture into at least three fractions in a single distillation step.

The invention also relates to phenol that is obtained using a process as claimed in at least one of claims 1 to 14.

The invention also relates to acetone that is obtained using a process as claimed in at least one of claims 1 to 14.

The advantage of the inventive process is that the separation steps chosen in the distillation substantially simplify a further work-up of the cleavage product mixture or of the individual fractions which are obtained from the cleavage product mixture. In particular, the combined removal of hydroxyacetone, AMS and cumene from the phenol-containing residue of the cleavage product mixture considerably simplifies the work-up of the phenol-containing residue, since the steps that are carried out in conventional processes in which the hydroxyacetone remains in the phenol-rich fraction and is removed from this by the hydroxyacetone being reacted with phenol to form compounds having a higher boiling point than phenol and which can be separated from phenol by distillation, are omitted and the steam consumption is lower in the resolution into said separation steps.

Compared with customary processes, the inventive process has a substantially more favorable energy balance and, compared with processes in which hydroxyacetone is removed from the process by reaction with phenol, also has a higher overall yield of phenol, based on the phenol content in the cleavage product mixture. The customary procedure requires a relatively high energy consumption. In addition, in customary processes, the yield of phenol is decreased, since the hydroxyacetone reacts to exhaustion with the phenol, or expensive chemicals, for example amines, must be added, which must themselves, or their reaction products, be removed again from the process in a complex manner.

The inventive process which avoids this problem by separating off the hydroxyacetone together with the cumene from the cleavage product mixture also requires a considerably smaller amount of equipment, since the separation of the cleavage product mixture into three fractions in a single distillation step decreases not only the number of the required distillation columns, but also the number of reaction apparatuses which are required to decrease the content of the various byproducts in the fractions.

Depending on the way the individual process steps are carried out, that is to say oxidation, cleavage with possible post-heating and hydrogenation, the steam consumption over the entire process per kg of phenol can be markedly decreased by employing the inventive process, compared with customary processes for which a consumption of 3.2 kg of steam/kg of phenol is quoted (from: Phenol/Acetone/Cumene, 96/97-2, from Chem Systems, 303 South Broadway, Tarrytown, N.Y. 10591). By means of the inventive process the energy consumption for the preparation of phenol which is suitable in each case for preparing bisphenol A can be markedly decreased. Also, depending on the way in which the individual abovementioned process steps are carried out, the yield of phenol in relation to the cumene used can be markedly increased, compared with processes in which HA is reacted with phenol to form high-boilers.

For the purposes of the present invention, the total number of plates present in a column is defined as 100% separation potential, independently of the number of plates, in order, in this manner, in the case of columns having a different number of plates, to be able to specify the range in which a similar separation potential is present. The bottom of the column, that is to say the region below the first plate, therefore has a separation potential of 0%. At the top of the column, that is to say in the range above the uppermost plate, in accordance with the definition, there is a separation potential of 100%. In accordance with this definition, a column having 50 plates has a separation potential of 30% in the region of the 15th plate.

The inventive process can be used for the work-up by distillation of mixtures of substances produced as cleavage product mixtures in the cleavage of alkylaryl hydroperoxides, in particular in the cleavage of cumene hydroperoxide into acetone and phenol. The cleavage product mixtures can be obtained by homogeneous or heterogeneous catalysis. Preferably, the inventive process is applied to cleavage product mixtures which are obtained by a homogeneous, acid-catalyzed cleavage. The acid homogeneous catalyst customarily used is sulfuric acid. The alkylaryl hydroperoxides can have been prepared in various ways known to chemists. Preferably, the inventive process, however, is applied to cleavage product mixtures which originate from the cleavage of alkylaryl hydroperoxides, in particular from the cleavage of cumene hydroperoxide (CHP), which have been obtained according to the principle of the Hock phenol synthesis [H. Hock, S. Lang, Ber. Dtsch. Chem. Ges. 77B, 257 (1944)]. Obviously, the inventive process can also be applied to cleavage product mixtures which are obtained by processes which are developments of the Hock process, in particular developments of the process steps oxidation and cleavage.

If acid is used as catalyst for the cleavage of alkylaryl hydroperoxides, in particular of CHP, the cleavage product mixture is usually, before the work-up by distillation, adjusted to a pH of 3 to 10, preferably of 4 to 7. This is achieved in the manner known to those skilled in the art by adding a base to the cleavage product mixture. The base can be, depending on operating conditions, a byproduct from the overall process, for example a phenoxide lye, an alkaline wash solution, as produced, for example, during the acetone washing, an inorganic base, for example sodium hydroxide solution, NaOH, ammonia or ammonium hydroxide or an organic base, for example an amine or diamine, for example hexamethylenediamine.

The pH can also be adjusted by using ion exchange resins before the work-up by distillation. Such resins and the use of such resins are known to those skilled in the art.

On account of the cleavage reaction, but also due to addition of catalyst or neutralizing agent, cleavage product mixtures usually contain a portion of water. This water can be removed in the manner known to those skilled in the art, before the cleavage product mixture is fed to the inventive process, by adding further water or removing an aqueous phase from the cleavage product mixture. Preferably, the aqueous phase is removed from the cleavage product mixture in at least one phase-separation apparatus, for example a separation vessel or a coalescer. Very particularly preferably, a cleavage product mixture which is to be worked up by distillation using the inventive process has a water content of 1 to 14% by weight, preferably from 6 to 10% by weight.

From the neutralization or owing to the use of salt-containing process streams, the cleavage product mixture can contain salts, in particular sodium salts or organic ammonium salts. Usually these are removed when the aqueous phase containing them is separated off from the organic part of the cleavage product phase. To carry out the inventive process it is advantageous (because of the reduction of salt deposits on heat exchangers; fouling), if the cleavage product mixture, before the inventive work-up by distillation, is treated in a manner known to those skilled in the art such that the sodium ion content is less than 200 ppm, preferably less than 50 ppm.

The inventive process is described hereinafter using as example the work-up by distillation of a cleavage product mixture produced in the homogeneous acid-catalyzed cleavage of CHP, without the process being restricted to this mode of carrying it out.

This cleavage product mixture can, depending on how the process steps oxidation, cleavage with possible post-heating, neutralization and/or phase separation into aqueous and organic phases are carried out, in addition to water and the main products phenol and acetone and the starting material cumene which is unreacted in the oxidation, also comprise various byproducts, for example α-methylstyrene (AMS), acetophenone, hydroxyacetone (HA), phenylbutenes, 3-methyl-cyclopentane, dimethylphenyl carbinol (DMPC), methyl-benzofuran (MBF), mesityl oxide (MO) and other carbonyl compounds, for example hexanone, heptanone and 2-phenylpropionaldehyde. Preferably, the cleavage product mixture comprises at least 20 to 70% by weight of phenol, 15 to 45% by weight of acetone, 5 to 30% by weight of cumene, 1 to 5% by weight of AMS and 200 ppm to 5% by weight of HA.

According to the invention the cleavage product mixture is resolved into at least three fractions in a single distillation step. This is preferably achieved by transferring the cleavage product mixture into a distillation apparatus, preferably a distillation column, which is dimensioned such that resolution of the cleavage product mixture into three fractions is possible.

Very particularly preferably, the cleavage product mixture is resolved into three fractions such that at least one fraction comprises at least 75%, preferably at least 95%, of a ketone present in the cleavage product before the distillation step. When a cleavage product mixture from the cleavage of CHP is used, this ketone is acetone. Preferably, at least one second fraction is obtained which comprises at least 75%, preferably at least 95%, of a substituted and/or unsubstituted phenol present in the cleavage product before the distillation step.

A third fraction obtained in the inventive work-up by distillation of a cleavage product mixture preferably comprises at least 75%, particularly preferably at least 95%, of the mono-, di- and/or trialkyl-substituted benzene used present in the cleavage product before the distillation step. In the case of work-up by distillation of a cleavage product mixture from the cleavage of CHP, this third fraction preferably comprises at least 75%, particularly preferably at least 95%, of the cumene present in the cleavage product before the distillation step and at least 75%, particularly preferably at least 95%, of the α-methylstyrene present in the cleavage product before the distillation step.

The first fraction which comprises the ketone, or acetone, is preferably removed at the top of the distillation column. The second fraction which comprises the substituted or unsubstituted phenol is preferably taken off at the bottom of the column. The third fraction, which comprises the unreacted mono-, di- and/or trialkyl-substituted benzene used in the oxidation, and when phenol is prepared comprises the cumene, is taken off from a side stream takeoff of the distillation column. Preferably, the side stream takeoff is situated above the feed of cleavage product mixture into the column, which is also performed at the side.

The inventive process for work-up by distillation is preferably carried out such that the bottom temperature in the distillation column is 140° C. to 200° C., particularly preferably 170 to 190° C. The temperature at the top of the column is preferably 30 to 90° C., particularly preferably 38 to 58° C. The temperature in the column interior in the region of the side stream takeoff is preferably 60 to 120° C., particularly preferably 65 to 90° C.

It can be advantageous to feed back into the distillation column as reflux a portion of the three fractions taken off from the column from the top, from the bottom and/or from the side stream takeoff.

The recycle from the bottom into the column is preferably heated via a heat exchanger, in which case the heating medium used can be steam or a process stream having sufficient thermal energy. The recycle ratio, defined as the amount of bottoms product recycled in the vapor state divided by the amount of bottoms product removed is preferably 0 to 10.

The reflux of the overhead product taken off at the top in the vapor state is preferably condensed by a heat exchanger and returned as liquid to the distillation column. The reflux ratio, defined as the amount of overhead product returned in the liquid state divided by the amount of overhead product removed is preferably 0.2 to 20, particular preferably 2 to 4.

In the case of the fraction taken off from the side stream takeoff, which can comprise water and can be divided into two phases in a phase separation apparatus, it can be advantageous to recycle as reflux to the column the organic portion of this fraction, the aqueous portion of this fraction or a mixture of organic and aqueous portions. Very particularly preferably, the aqueous portion and the organic portion of this fraction are recycled separately to the distillation column. The reflux ratio based on the amount of recycled water and the amount of water taken off is preferably 0.2 to 3, very particularly preferably from 0.4 to 2. The water which is recirculated to the column can be fed into the column in the liquid or vapor state, preferably in the liquid state. The reflux ratio based on the amount recirculated and the amount of organic phase taken off is preferably 0.1 to 10, very particularly preferably 0.5 to 5. The remainder of the organic portion of this third fraction obtained from the phase-separation apparatus is fed to further work-up, as is the fraction taken off at the top and bottom of the distillation column. The remainder of the aqueous portion of the third fraction obtained from the phase-separation apparatus is fed to work-up or disposal.

However, it can also be advantageous to feed back a portion of the water provided for the work-up or disposal into the column in the vapor state, using a heat exchanger. The material is preferably fed in below the point at which the cleavage product is fed into the distillation column.

Further work-up of the three fractions obtained in the first distillation step is preferably performed as work-up by distillation and can be performed as already described in the prior art. The work-up can be performed in particular adapted to the composition of the fractions. Depending on the procedure of the inventive process, interfering impurities, in particular hydroxy ketones, can be present in the second and/or third fraction. If the hydroxy ketones, for example hydroxyacetone, are present in the second fraction, this fraction can be separated off, for example from phenol, by the various processes described in the prior art.

In a particularly preferred embodiment of the inventive process, this is operated in such a manner that the inventive third fraction comprises at least 20%, preferably at least 50%, and very particularly preferably at least 90%, of the hydroxy ketones present in the cleavage product before the distillation step. In the case of work-up by distillation of a cleavage product mixture from the cleavage of CHP, this third fraction preferably comprises at least 90% of the hydroxyacetone present in the cleavage product before the distillation step.

The advantage of this type of carrying out the inventive process is that the hydroxyacetone which is present in the third fraction accumulates in the water of this fraction. The hydroxyacetone predominantly passes over into the aqueous phase in the phase-separation apparatus and can thus be ejected from the process in a simple manner together with the aqueous portion of the third fraction. Preferably, the aqueous phase comprises at least 75%, particularly preferably 95%, and very particularly preferably 98%, of the hydroxyacetone present in the third cumene- and/or AMS-containing fraction.

It can be advantageous if the cleavage product mixture is resolved, not as described above into three main fractions, but into at least four main fractions. Such a fourth fraction can be taken off from a further side stream takeoff which is disposed above the side stream takeoff via which the third, cumene-containing fraction is taken off, and is disposed below the top of the column, and/or can be taken off from a further side stream takeoff which is disposed below the feed of the cleavage product mixture and above the bottom of the column, and comprises at least one organic acid. As organic acid, this fourth fraction can comprise, for example, acetic acid, oxalic acid, formic acid or butyric acid or a mixture consisting of at least one of these acids. Preferably, such fractions comprising at least one acid can be fed to a neutralization upstream of the work-up by distillation. It can be advantageous, to provide a plurality of such side stream takeoffs in order to be able to eject from the column these fractions which comprise acids having varying boiling points.

In a further particularly preferred type of carrying out the inventive process, the first fraction which, in the case of CHP cleavage, comprises at least 75% of the acetone present in the cleavage product mixture before the work-up by distillation, is transferred to an acetone column, preferably in the vapor state, preferably at the side. In this column the acetone is separated from impurities to the extent that it meets the requirements of pure acetone (meeting the permanganate test as specified in ASTM D 1363-94). Impurities present in the crude acetone before entry into the acetone column which come into question are in particular acetaldehyde as a compound having a lower boiling point than acetone and compounds which have a higher boiling point than acetone.

To remove the impurities, the acetone column must be designed in such a manner that the pure acetone can preferentially be taken off from a side stream takeoff while a fraction in which acetaldehyde accumulates may be taken off at the top of the column. This fraction can in part be recirculated directly to the acetone column, in which case a heat exchanger can be provided by which the acetaldehyde-enriched fraction can be completely or partly condensed. The reflux ratio, defined as the amount of reflux in the top divided by the amount of the side stream, is preferably 0.1 to 1000. Particularly preferably, the acetaldehyde-enriched fraction is transferred in whole or in part into a reaction apparatus, in which case a heat exchanger can likewise be provided, using which heat exchanger the acetaldehyde-enriched fraction can be condensed in whole or in part, in which reaction apparatus the fraction is brought into contact with a reaction partner which has alkaline properties, preferably with sodium hydroxide solution, and very particularly preferably with a 5 to 20% strength sodium hydroxide solution. The temperature in this reaction apparatus is preferably 20 to 60° C. The pressure in this reaction apparatus is preferably 0.1 to 2 bar. In this reaction apparatus the acetaldehyde reacts due to basic catalysis in an aldol condensation reaction, for example with itself, to form 3-hydroxybutyraldehyde (acetaldol) or with acetone to form hydroxypentanone. In particular the acetaldol and the hydroxypentanone have a higher boiling point than acetone. The reaction mixture from this reaction apparatus is recirculated to the acetone column at the side. A further portion of the overhead product of the acetone column can also be ejected directly from the process and fed to a work-up or thermal utilization.

At the bottom of the acetone column a mixture of compounds which have a higher boiling point than acetone is taken off. This bottoms product can comprise, inter alia, small amounts of cumene and/or AMS which are transferred into the acetone column with the first fraction from the first distillation column and comprise compounds from the reaction apparatus, in particular sodium hydroxide solution or water and the secondary products of acetaldehyde formed by aldol condensation reactions, for example acetaldol. It can be advantageous to recycle a portion of the bottoms product to the column in the vapor state. Preferably, the recycle ratio is 0.2 to 400. The residual portion of the bottoms product can be fed to work-up or utilization. In particular, it can be advantageous, to recover residues of cumene and/or AMS present in the bottoms product to feed the bottoms product or portions thereof into a cumene column in which cumene and AMS are enriched.

The acetone column is preferably operated such that at the top of the column a temperature of 30 to 60° C. is established. The bottom temperature is preferably 40 to 110° C., particular preferably 50 to 80° C. The temperature in the acetone column at the side stream takeoff from which the pure acetone is taken off is preferably 30 to 60° C. The acetone column preferably has 10 to 120 theoretical stages. The side stream takeoff from which the pure acetone is taken off is preferably in a region of the column in which this has a separation potential of 80 to 99%, preferably 90 to 95%. The crude acetone, that is to say the first fraction from the first distillation column, is preferably fed into a region of the acetone column where this has a separation potential of 0 to 30%. The reaction mixture from the reaction apparatus is preferably fed into a region of the acetone column where this has a separation column of 0 to 30%.

The organic portion of the third fraction from the phase-separation apparatus is transferred to a cumene column. This is preferably dimensioned in such a manner that compounds which have a lower boiling point than cumene and/or AMS, for example water or acetaldol, can be removed overhead, and compounds which have a boiling point which is above that of AMS and cumene can be removed at the bottom of the column and the compounds cumene and/or AMS can be taken off from a side stream takeoff. Preferably, not only a portion of the product taken off at the top but also of the product taken off at the bottom of the column are fed back into the column. Particularly preferably, the cumene column is dimensioned in such a manner and the process parameters are set in such a manner that a mixture taken off from the side stream takeoff or bottom region can be fed directly to the hydrogenation.

The cumene column is preferably operated in such a manner that a temperature of 40 to 170° C. is established at the top of the column. The bottom temperature is preferably 110 to 180° C. The temperature in the cumene column at the side stream takeoff from which the cumene and/or the AMS is taken off is preferably 110 to 180° C. The cumene column preferably has 10 to 90 theoretical stages. The side stream takeoff from which the cumene and/or AMS is taken off is preferably situated in the region of the column in which this has a separation potential of 0 to 50%. The organic phase of the third fraction from the first distillation column is preferably fed into a region of the cumene column where this has a separation potential of 10 to 80%.

It can also be advantageous to dimension the cumene column such that via at least one further side stream takeoff which is disposed above the side stream takeoff from which cumene and/or AMS is removed from the cumene column and below the top of the column, at least one further fraction can be taken off which comprises at least mesityl oxide, ketones and/or water. By providing one or more such additional side stream takeoffs, the overhead product in the cumene column obtained can be a product which essentially comprises acetone which is free from mesityl oxide and which can be fed to further work-up, for example in the acetone column.

The second fraction taken off at the bottom of the first distillation column, the crude phenol fraction, which has a hydroxyacetone content less than 500 ppm, preferably less than 100 ppm, and very particularly preferably less than 10 ppm, is preferably transferred at the side into a column which, in the further course, is termed the crude phenol column. This column is preferably dimensioned in such a manner that compounds which have a lower boiling point than phenol, for example residues of cumene, AMS or acetone, can be removed overhead, and compounds which have a boiling point above that of phenol can be taken off at the bottom of the column, and phenol can be taken off from a side stream takeoff. Preferably, not only a portion of the product taken off at the top but also of the product taken off at the bottom of the crude phenol column is recycled to the column. Particularly preferably, the crude phenol column is dimensioned in such a manner and the process parameters are set in such a manner that a phenol fraction withdrawn from the side stream takeoff can be fed to further phenol purification. It can also be advantageous in the case of the side stream takeoff to feed back a portion of the fraction taken off into the crude phenol column as reflux.

The crude phenol column is preferably operated in such a manner that at the top of the columns a temperature of 120 to 200° C., preferably 130 to 180° C., is set. The bottom temperature is preferably 120 to 220° C. The temperature in the crude phenol column at the side stream takeoff from which phenol is taken off is preferably 120 to 190° C., particular preferably 140 to 190° C. The crude phenol column preferably has 10 to 70 theoretical stages. The side stream takeoff from which the phenol is taken off is preferably in a region of the column in which this has a separation potential of 30 to 90%. The second fraction from the first distillation column, that is to say of the crude phenol, is preferably fed into a region of the crude phenol column where this has a separation potential of 0 to 80%.

It can be advantageous to recycle the overhead product of the crude phenol column to the first distillation column. This is useful, in particular, when the overhead product of the crude phenol column comprises relatively large amounts of cumene, AMS and/or acetone. The bottoms product of the crude phenol column, which comprises compounds that have a higher boiling point than phenol, can be fed, for further concentration of the high-boilers, to further distillation and/or cracking.

Despite the advantage that, in the case of cracking, valuable compounds, for example AMS or phenol, can be recovered, and thus the overall yield of the process is increased, it can be advantageous to dispense with cracking of the high-boilers, since the apparatus requirement and the energy consumption cannot always be compensated for by the higher overall yield.

Preferably, the bottoms product of the crude phenol column is transferred to a further distillation column which is termed below high-boiler column. The bottoms product from the crude phenol column is preferably fed in to the side of the high-boiler column. This column is preferably dimensioned such that compounds that have a boiling point in the region of the boiling point of phenol, for example residues of phenol, cumene, AMS or acetone, can be removed overhead, and compounds that have a boiling point markedly above that of phenol can be taken off at the bottom of the column. Preferably, not only a portion of the product taken off at the top but also of the product taken off at the bottom of the high-boiler column is recycled to the column. The reflux ratio for the overhead product is preferably 0.5 to 20. The bottoms product can be fed to cracking or preferably thermal utilization. The overhead product of the high-boiler column is preferably fed back into the crude phenol column.

The high-boiler column is preferably operated in such a manner that a temperature of 90 to 180° C. is set at the top of the columns. The bottom temperature is preferably 120 to 220° C. The high-boiler column preferably has 5 to 70 theoretical stages. The bottoms product from the crude phenol column is preferably fed into a region of the high-boiler column where this has a separation potential of 40 to 100%.

The phenol fraction taken off at the side stream takeoff of the crude phenol column can be fed to further work-up by distillation. Preferably, this phenol fraction is treated in advance in a reactor. The treatment preferably consists of a treatment with an acid catalyst in order to convert unwanted byproducts into compounds boiling higher or lower than phenol. Very particularly preferably, acid ion exchangers are used as acid catalysts.

For the further work-up by distillation of the phenol fraction from the crude phenol column, this is transferred treated or untreated into a distillation column which is termed below pure phenol column. This column is preferably dimensioned such that compounds that have a lower boiling point than phenol, for example residues of cumene, AMS, acetone and/or water, can be removed overhead, and compounds that have a boiling point above that of phenol can be taken off at the bottom of the column and phenol can be taken off from a side stream takeoff. Preferably, not only a portion of the product taken off at the top but also of the product taken off at the bottom of the crude phenol column is recycled to the column. The reflux ratio, defined as the amount of reflux at the top divided by the amount in the side stream is preferably 0.1 to 1000. The recycle ratio for the bottoms product is preferably 0.1 to 40. Particularly preferably, the pure phenol column is dimensioned in such a manner and the process parameters set in such a manner that a pure phenol fraction withdrawn from a side stream takeoff has an impurity content less than 0.01% by weight, preferably less than 0.005% by weight. This pure phenol can be fed to a store or directly for further use.

The pure phenol column is preferably operated such that a temperature of 100 to 190° C. is set at the top of the columns. The bottom temperature is preferably 120 to 210° C. The temperature in the pure phenol column at the side stream takeoff from which the pure phenol is taken off is preferably 100 to 190° C. The pure phenol column preferably has 10 to 70 theoretical stages. The side stream takeoff from which the pure phenol is taken off is preferably situated in the region of the column in which this has a separation potential of 80 to 95%. The phenol fraction from the crude phenol column is preferably fed into a region of the pure phenol column where this has a separation potential of 10 to 80%, but not in the region of the column which has the same separation potential as the region from which the pure phenol is withdrawn.

It can be advantageous to recycle the overhead product of the pure phenol column to the crude phenol column. This is useful, in particular, because the overhead product of the pure phenol column frequently comprises cumene, AMS and/or acetone. The bottoms product of the pure phenol column which comprises compounds that have a higher boiling point than phenol can also be fed back into the crude phenol column or fed for further concentration of the high-boilers to further distillation and/or cracking.

The inventive process can be carried out at a pressure of 0.05 to 2 bar. Depending on the established pressure at which the individual process steps are carried out, the temperatures in these process steps must be selected accordingly.

The inventive process can [lacuna] in an inventive process for preparing phenol and acetone which comprises the steps
oxidation of cumene to cumene hydroperoxide
cleavage of cumene hydroperoxide
work-up by distillation of the cleavage product mixture produced in the cleavage of cumene hydroperoxide and which comprises resolving the cleavage product mixture into at least three fractions in a single distillation step. By means of such an inventive process phenol can be prepared in a very favorable manner in terms of energy.

The inventive process for the work-up by distillation of a cleavage product mixture produced in the cleavage of an alkylaryl hydroperoxide, in particular in the cleavage of CHP, is preferably carried out in an inventive distillation column for separating by distillation cleavage product mixtures from the cleavage of cumene hydroperoxide, in which the column is dimensioned in such a manner that a crude acetone fraction comprising at least 75% by weight of acetone can be taken off at the top of the column, a crude phenol fraction comprising at least 75% by weight of phenol can be taken off at the bottom of the column and a fraction which comprises at least hydroxyacetone and cumene and/or α-methylstyrene can be taken off from the side of the column.

The inventive distillation column preferably has a number of theoretical stages of 20 to 200, particularly preferably 30 to 70. The total number of trays present in the distillation column is defined for the purposes of the present invention, independently of the number of trays, as 100% separation potential, in order in this manner, in the case of columns having a differing number of trays, to be able to specify the range at which a similar separation potential is present. The bottom of the column, that is to say the region below the first tray, therefore has a separation potential of 0%. At the top of the column, that is to say the region of the uppermost tray, in accordance with the definition, a separation potential of 100% is present.

The inventive distillation column has at least one possible feed which is preferably present in a region of the distillation column in which this has a separation potential of 20 to 50%.

The inventive distillation column also has at least one side stream takeoff at which a fraction which comprises at least one hydroxyacetone, that is in the case of cleavage of CHP, hydroxyacetone, and a mono- or polyalkylated benzene, in the case of cleavage of CHP, that is cumene and/or α-methylstyrene, can be taken off. Preferably, this side stream takeoff is installed at a region of the distillation column at which the separation potential is 15 to 95%, preferably 60 to 90%. Thus the side stream takeoff, in the case of an inventive column which has a number of theoretical stages of 50, is preferably installed between the thirtieth and forty-fifth stage.

It can be advantageous if the inventive distillation column has at least one further side stream takeoff at which a fraction which comprises at least one organic acid can be taken off. As organic acid the fraction can comprise, for example, acetic acid, oxalic acid, formic acid or butyric acid, or a mixture consisting of at least one of these acids. An acid takeoff can be provided above and/or below the feed means and/or below and/or above the side stream takeoff.

Figure 2:
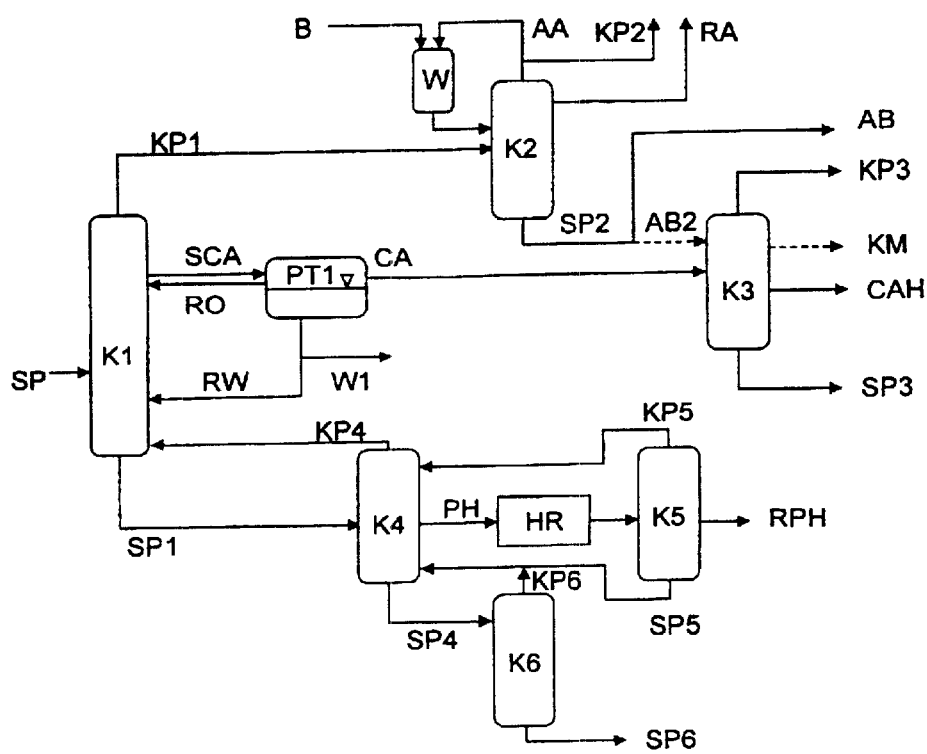

The inventive process and the inventive apparatus are described in the drawings FIGS. 1 and 2 by way of example, without the process or the apparatus being restricted to these types of implementation.

FIG. 1 shows diagrammatically an embodiment of the inventive distillation column. The inventive distillation column K1 has a side intake into which cleavage product mixture SP can be fed for work-up by distillation. The overhead product KP1 and the bottoms product SP1 can be taken off at the top and bottom of the column, respectively. The inventive distillation column has in each case reflux systems by which the bottoms product and/or the overhead product can be returned to the column in whole or in part. In these reflux systems the heat exchangers WT1 and WT2 are installed, by means of which it is possible to add or remove heat energy to the bottoms product or overhead product recycled as reflux to the column. If, in the inventive distillation column, a cleavage product mixture which originates from the cleavage of CHP is worked up by distillation, acetone is enriched in the overhead product. In the bottoms product predominantly phenol is enriched, and compounds having a boiling point higher than phenol.

The inventive distillation column furthermore has a side stream takeoff via which a fraction that has a boiling point between that of the overhead product and that of the bottoms product is taken off from the column. If, in the inventive column, a cleavage product mixture from the cleavage of CHP is worked up by distillation, via this side stream takeoff a mixture which can comprise at least cumene, AMS and/or water is ejected from the column. This mixture is transferred via line SCA to a phase-separation apparatus PT1, for example a decanter. A portion of the organic phase formed in this phase-separation apparatus can be returned via RO to the distillation column. The residual portion of the organic phase can be fed to further work-up via CA. A portion of the aqueous phase can also be returned to the distillation column K1 via RW1, preferably this aqueous phase is returned to the column in the liquid state. The residual portion of the aqueous phase can be fed via W1 to utilization or work-up.

Optionally, a further portion of the aqueous phase can be returned to the column via RW2 in the vapor state or liquid state, in which case the aqueous phase is preferably fed in below the feed of the cleavage product mixture SP. Optionally, one or more further side stream takeoffs SOS1 and SOS2 can be provided. The side stream takeoff SOS1 is preferably disposed between the feed of the cleavage product mixture SP and the bottom of the column. The side stream takeoff SOS2 is preferably disposed between the side stream takeoff SCA and the top of the column. Fractions that have at least one organic acid can be ejected from the column via the side stream takeoffs SOS1 and SOS2.

FIG. 2 shows a diagrammatic representation of the overall process for the work-up by distillation of cleavage product mixtures produced in the cleavage of alkylaryl hydroperoxides, for example a cleavage product mixture produced in the cleavage of CHP. The representation, for improved clarity, does not show the various refluxes to the columns. Also, the thermal circuit, that is to say the exchange of heat energy between the individual fractions or process streams, is not shown.

Via SP, a cleavage product mixture passes for work-up distillation into column K1. The cleavage product mixture can have already been treated, for example the pH can have been set and/or any aqueous phase present can already have been removed. In the column K1 the cleavage product mixture is divided into three fractions. The overhead product KP1 taken off at the top of the column is a fraction in which acetone is enriched. A side stream fraction SCA in which cumene, AMS and/or water are enriched is taken off at the side from column K1. A phenol-rich bottoms product SP1 is taken off at the bottom of column K1.

This fraction is transferred into the side of the acetone column K2 in which the overhead product KP1 is resolved in a pure acetone fraction RA, which is taken off at the side below the top of the column, an aldehyde- and low-boiler-containing fraction AA, which is taken off at the top of the column, and a bottoms fraction SP2, which is taken off at the bottom of the column and which comprises compounds having a boiling point which is higher than that of acetone. The fraction AA is fed in part into a washer W, into which a base B is also fed, or is ejected from the process via KP2. The product taken off from the washer W is fed back into the column K2. The pure acetone RA is fed to further utilization or storage. The bottoms product SP2 can be fed, for example, to work-up AB, in particular to wastewater treatment. A portion of the worked-up bottoms product AB2 can be fed into the side of column K3.

In addition, the organic portion CA of the side stream fraction SCA from column K1 is fed into column K3. This organic portion is obtained in a phase-separation apparatus PT1, into which the side stream fraction is fed. A portion RO of the organic portion of the side stream fraction is recycled to the column K1. The aqueous portion of the side stream fraction obtained in the phase-separation apparatus PT1 can either be ejected from the process as process water W1 and/or can be recycled in whole or in part to the column K1 as reflux RW.

In column K3 the organic portion of the side stream fraction from column K1, which comprises cumene and/or AMS, is distilled in such a manner that, via a side stream takeoff from column K3, a fraction CAH is obtained which comprises cumene and AMS and is suitable for being fed directly to the hydrogenation of AMS to cumene. Compounds boiling higher than AMS or lower than cumene are ejected from the overall process as overhead product KP3 or as bottoms product SP3, and can be fed for utilization. Optionally, one or more side stream takeoffs KM can be provided above the side stream takeoff CAH and below the top of the column K3, via which side stream takeoffs fractions can be taken off that comprise at least mesityl oxide and/or ketones, in particular ketones different from acetone.

The phenol-rich bottoms product SP1 from column K1 is fed into the side of crude phenol column K4. From this column a crude phenol is taken off at the side which is further treated in a reactor HR which can comprise, for example, an acid fixed-bed catalyst, and is then transferred to the column K5. The overhead product KP4 is fed back into the column K1. The bottoms product SP4 from column K4 is fed into column K6. In this column, high-boilers, for example tar, are ejected from the process as bottoms product SP6 and fed for utilization. The overhead product KP6 is fed back into the column K4.

The crude phenol which was treated in reactor HR and transferred to the pure phenol column K5 is separated in this column into pure phenol RPH which is withdrawn at the side of column K5 and fed for use or storage, a higher-boiling fraction which is taken off from K5 as bottoms product SP5 and recycled to column K4, and a lower-boiling fraction which is withdrawn from column K5 as overhead product KP5 and is also fed to column K4.

EXAMPLE 1

A cleavage product mixture which comprised, inter alia, 48% by weight of phenol, 10% by weight of cumene, 3% by weight of AMS, 27% by weight of acetone, 0.03% by weight of acetaldehyde, 0.1% by weight of acetophenone, 0.1% by weight of hydroxyacetone and 9% by weight of water was fed into a distillation column as described in FIGS. 1 and 2, that had 90 trays, at the height of the 40th tray.

The temperature in the column was set such that the top temperature was 47° C., the bottom temperature was 179° C. and the temperature at the side stream takeoff was 88 to 89° C. The pressure in the distillation column corresponded at the bottom to atmospheric pressure. A portion of the overhead product taken off, which comprised, inter alia, 99 parts of acetone and 0.1 part of acetaldehyde, was transferred to an acetone column having 40 trays, at the height of the 8th tray.

The temperature in the acetone column was set in such a manner that the temperature at the top of the column was 42° C. and the temperature at the bottom of the column was 65° C. At the side stream takeoff, which was mounted at the height of the 35th tray, and from which pure acetone that had an impurity content less than 0.25% by weight was taken off, the temperature was 42.5° C. The overhead product which had an acetaldehyde content of 100 ppm was condensed and passed into a washer, into which were also passed, per kg of overhead product, 10 g of a 5% strength sodium hydroxide solution. The temperature in the washer was 56° C. The mixture taken off from the washer had an acetaldehyde content less than 20 ppm.

The bottoms product from the acetone column, which comprised, inter alia, cumene, AMS and water, was transferred to the cumene column.

The fraction taken off from the side stream takeoff of the first distillation column was transferred to a separation vessel. In this separation vessel, an aqueous phase which comprised, inter alia, 98% by weight of water and 1.3% by weight of hydroxyacetone, was separated from the organic phase which comprised, inter alia, 65% by weight of cumene, 30% by weight of AMS, 2% by weight of phenol and 0.2% by weight of water. After the phase separation, over 95% of the hydroxyacetone present in the fraction taken off was present in the aqueous phase. A portion of the aqueous phase was discarded. The remainder of the aqueous phase was returned to the first distillation column.

The organic phase separated off in the separation vessel from the aqueous phase had a hydroxyacetone content less than 1000 ppm. This organic phase was in part returned into the first distillation column. The remainder of the organic phase was passed into the side of the cumene column which had 60 trays, at the height of the 25th tray. The cumene column was operated such that the temperature at the top of the column was 56° C. and the temperature at the bottom of the column was 140° C. From a side stream takeoff at the height of the 14th tray, at 138° C. a mixture of AMS and cumene was distilled off, which comprised less than 2% by weight of impurities. The low-boilers and high-boilers taken off at the top and from the bottom of the cumene column were discarded.

The bottoms product taken off from the bottom of the first distillation column, which comprised, inter alia, 94% by weight of phenol and 1.6% of acetophenone, was fed into the side of a crude phenol column comprising 70 trays at the height of the 26th tray. This column was operated in such a manner that the temperature at the top of the column was 176° C. and the temperature at the bottom of the column was 203° C. The fraction taken off at the top of the crude phenol column was returned to the first distillation column. The fraction produced in the bottom of the crude phenol column was transferred to a further column, the high-boiler column, in which the high-boilers were concentrated. The overhead product of this 50-tray column obtained at 154° C. was a fraction which comprised, inter alia, 95% by weight of phenol and 5% by weight of acetophenone. This fraction was fed back into the crude phenol column. The bottoms product of the high-boiler column, which was obtained at a temperature of 203° C., consisted of a tar, which had a phenol content of less than 5% by weight. A crude phenol stream was taken off from the crude phenol column at the height of the 55th tray, at a temperature of 181° C.

This crude phenol stream had a phenol content of 99% by weight. As impurities, this crude phenol stream comprised, inter alia, 2-methylbenzofuran, AMS, mesityl oxide, small amounts of hydroxyacetone and traces of further impurities. This crude phenol stream was passed through a reactor which comprised 120 m$^3$ of the acid ion exchange resin Amberlyst 15 as catalyst. The crude phenol thus treated was passed into the side of a 45-tray pure phenol column at the height of the 20th tray. This column, which was operated at a reduced pressure, had a top temperature of 139° C. and a bottom temperature of 142° C. A pure phenol that had an impurity content less than 100 ppm was taken off from the side of the pure phenol column at the height of the 40th tray at a temperature of 140° C. The fraction taken off at the top of the pure phenol column was fed back into the crude phenol column below the top. The fraction taken off from the bottom of the pure phenol column was fed back into the crude phenol column above the bottom.

What is claimed is:

1. A process for the work-up by distillation of cleavage product mixtures produced in the cleavage of alkylaryl hydroperoxides, which comprises resolving the cleavage product mixture into at least three fractions in a single distillation step, wherein said work-up by distillation is performed in a distillation column.

2. The process as claimed in claim 1, wherein one of the fractions comprises at least 75% of a ketone present in the cleavage product before the distillation step.

3. The process as claimed in claim 2, wherein the ketone is acetone.

4. The process as claimed in claim 1, wherein one of the fractions comprises at least 75% of a substituted and/or unsubstituted phenol present in the cleavage product before the distillation step.

5. The process as claimed in claim 1, wherein one of the fractions comprises at least 75% of cumene present in the cleavage product before the distillation step and/or 75% of α-methylstyrene (AMS) present in the cleavage product before the distillation step.

6. The process as claimed in claim 5, wherein this fraction, which comprises water, cumene and/or AMS, comprises at least 20% of hydroxyacetone present in the cleavage product before the distillation step.

7. The process as claimed in claim 5, wherein the fraction comprising at least 75% of the cumene present in the cleavage product before the distillation step and/or 75% of the α-methylstyrene present in the cleavage product before the distillation step is separated in a phase-separation apparatus into an aqueous phase and an organic phase.

8. The process as claimed in claim 7, wherein at least a portion of the organic phase is fed back to the distillation step.

9. The process as claimed in claim 7, wherein at least a portion of the organic phase is fed to a cumene distillation column in which the organic phase is separated in such a manner that compounds are taken off overhead which have a lower boiling temperature than cumene or α-methylstyrene, compounds are taken off via the bottom which have a higher boiling temperature than cumene or α-methylstyrene and the compounds cumene and/or α-methylstyrene are taken off via a side stream takeoff.

10. The process as claimed in claim 9, wherein the organic phase is separated in the cumene column in such a manner that, via at least one further side stream takeoff which is disposed above the side stream takeoff from which cumene and/or α-methylstyrene are removed from the cumene column, and below the top of the column, at least one further fraction can be taken off which comprises at least mesityl oxide, ketones and/or water.

11. The process as claimed in claim 7, wherein at least a portion of the aqueous phase is fed back to the distillation step in the liquid and/or vapor state.

12. The process as claimed in claim 7, wherein the aqueous phase comprises 75% of the hydroxyacetone present in the cumene- and/or α-methylstyrene-containing fraction.

13. The process as claimed in claim 1, wherein the cleavage product mixture, before the work-up by distillation, has a phenol concentration of 20 to 70% by weight.

14. The process as claimed in claim 1, wherein the cleavage product mixture, before the work-up by distillation, has a hydroxyacetone concentration of 200 ppm to 5% by weight.

15. The process as claimed in claim 1, wherein said work-up by distillation is performed in a distillation column in which the column is dimensioned such that a crude acetone fraction comprising at least 75% by weight of acetone can be taken off at the top of the column, a crude phenol fraction comprising at least 60% by weight of phenol can be taken off at the bottom of the column and at least one fraction which comprises at least water, cumene and/or α-methylstyrene can be taken off from the side of the column.

16. The process as claimed in claim 15, wherein the column is dimensioned such that a fraction comprising phenol and at least 75% of the hydroxyacetone present in the cleavage product mixture can be taken off at the bottom of the column.

17. The process as claimed in claim 15, wherein the column is dimensioned such that a fraction comprising cumene and/or α-methylstyrene and at least 75% of the hydroxyacetone present in the cleavage product mixture can be taken off at at least one side stream takeoff of the column.

18. The process as claimed in claim 17, wherein the column is provided with a side stream takeoff at which a fraction which comprises at least hydroxyacetone and cumene and/or α-methylstyrene can be taken off in a region of the column in which this has a separation potential of 15 to 95%.

19. The process as claimed in 15, wherein the column has 20 to 200 theoretical stages.

20. The process as claimed in claim 15, wherein the column has at least one side stream takeoff at which a fraction which comprises at least one organic acid can be taken off.

21. A process for preparing phenol and acetone which comprises oxidizing cumene to cumene hydroperoxide;

cleaving cumene hydroperoxide; and working-up the cleavage product mixture produced by the cleavage of cumene hydroperoxide, which comprises resolving the cleavage product mixture into at least three fractions in a single distillation step, wherein said work-up is by distillation performed in a distillation column.

22. The process according to claim 21, wherein said distillation column is dimensioned such that a crude acetone fraction comprising at least 75% by weight of acetone can be taken off at the top of the column, a crude phenol fraction comprising at least 60% by weight of phenol can be taken off at the bottom of the column and at least one fraction which comprises at least water, cumene and/or α-methylstyrene can be taken off from the side of the column.

23. The process according to claim 1, wherein said distillation column is dimensioned such that a crude acetone fraction comprising at least 75% by weight of acetone can be taken off at the top of the column, a crude phenol fraction comprising at least 60% by weight of phenol can be taken off at the bottom of the column and at least one fraction which comprises at least water, cumene and/or α-methylstyrene can be taken off from the side of the column.

24. The process as claimed in claim 6, wherein the fraction comprising at least 75% of the cumene present in the cleavage product before the distillation step and/or 75% of the α-methylstyrene present in the cleavage product before the distillation step is separated in a phase-separation apparatus into an aqueous phase and an organic phase.

25. The process as claimed in claim 24, wherein at least a portion of the organic phase is fed back to the distillation step.

26. The process as claimed in claim 25, wherein at least a portion of the organic phase is fed to a cumene distillation column in which the organic phase is separated in such a manner that compounds are taken off overhead which have a lower boiling temperature than cumene or α-methylstyrene, compounds are taken off via the bottom which have a higher boiling temperature than cumene or α-methylstyrene and the compounds cumene and/or α-methylstyrene are taken off via a stream takeoff.

27. The process as claimed in claim 26, wherein the organic phase is separated in the cumene distillation column in such a manner that, via at least one further side stream takeoff which is disposed above the side stream takeoff from which cumene and/or α-methylstyrene are removed from the cumene distillation column, and below the top of the column, at least one further fraction can be taken off which comprises at least mesityl oxide, ketones and/or water.

28. The process as claimed in claim 25, wherein at least a portion of the aqueous phase is fed back to the distillation step in the liquid and/or vapor state.

29. The process as claim 28, wherein the aqueous phase comprises 75% of the hydroxyacetone present in the cumene- and/or α-methylstyrene-containing fraction.

* * * * *

UNITED STATES PATENT AND TRADEMARK OFFICE
CERTIFICATE OF CORRECTION

PATENT NO.     : 6,657,087 B2
DATED          : December 2, 2003
INVENTOR(S)    : Markus Weber et al.

It is certified that error appears in the above-identified patent and that said Letters Patent is hereby corrected as shown below:

<u>Column 19,</u>
Lines 27 and 29, "15" should read -- claim 15 --

<u>Column 20,</u>
Line 42, "as claim 28" should read -- as claimed in claim 28 --

Signed and Sealed this

Twenty-fifth Day of May, 2004

JON W. DUDAS
*Acting Director of the United States Patent and Trademark Office*